United States Patent [19]

Hoehn

[11] 4,260,614
[45] Apr. 7, 1981

[54] 4-(2-(1H-IMIDAZOL-1-YLMETHYL)-1,3-DIOXOLAN-4-YL)METHOXYPYRAZOLO(3,4-B)PYRIDINES

[75] Inventor: Hans Hoehn, Tegernheim, Fed. Rep. of Germany

[73] Assignee: E. R. Squibb & Sons, Inc., Princeton, N.J.

[21] Appl. No.: 119,908

[22] Filed: Feb. 8, 1980

[51] Int. Cl.³ .................. C07D 471/02; A61K 31/435
[52] U.S. Cl. ..................................... 424/256; 546/119; 546/120
[58] Field of Search ................. 546/119, 120; 424/256

[56] References Cited

U.S. PATENT DOCUMENTS

| 3,936,470 | 2/1976 | Heeres | 424/273 X |
|---|---|---|---|
| 4,101,664 | 7/1978 | Heeres | 424/273 R |
| 4,101,665 | 7/1978 | Heeres | 424/273 X |
| 4,101,666 | 7/1978 | Heeres | 424/273 X |
| 4,139,540 | 2/1979 | Heeres | 260/340.9 R |
| 4,159,380 | 1/1979 | Hoehn | 546/119 |

OTHER PUBLICATIONS

Heeres et al., J. Med. Chem. 22 (8), 1979, pp. 1003–1005.

Primary Examiner—Joseph P. Brust
Attorney, Agent, or Firm—Lawrence S. Levinson; Burton Rodney

[57] ABSTRACT

Compounds are provided having the formula

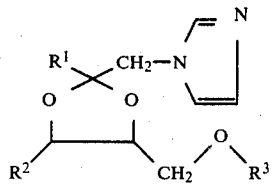

wherein
R¹ is hydrogen, lower alkyl; substituted or unsubstituted phenyl-lower alkyl; substituted or unsubstituted phenyl; substituted or unsubstituted 5- or 6-membered monocyclic aromatic heterocyclic containing one O, S or N atom; in the above substituted groups, the phenyl groups bear one or two substituents and the heterocyclic bears one substituent which may be a halogen, hydroxy, lower alkyl, lower alkoxy, lower alkylthio, cyano or nitro group;
R² is hydrogen, lower alkyl, or substituted or unsubstituted phenyl; and
R³ is substituted 1H-pyrazolo[3,4-b]pyridine or substituted 2H-pyrazolo[3,4-b]pyridine The above compound as well as their physiologically acceptable acid-addition salts are useful as antimicrobial agents, especially, antifungal agents.

13 Claims, No Drawings

4-(2-(1H-IMIDAZOL-1-YLMETHYL)-1,3-DIOXO-LAN-4-YL)METHOXYPYRAZOLO(3,4-B)PYRI-DINES

SUMMARY OF THE INVENTION

This invention relates to new 4-[2-(1H-imidazol-1-ylmethyl)-1,3-dioxolan-4-yl]methoxy pyrazolo[3,4-b]pyridines and the acid-addition salts of these compounds. These new compounds have the formula

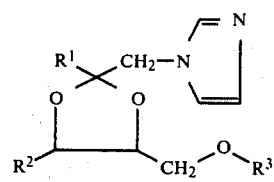

The symbols have the following meaning in formula I and throughout the specification:

$R^1$ is hydrogen, lower alkyl; substituted or unsubstituted phenyl-lower alkyl; substituted or unsubstituted phenyl; substituted or unsubstituted 5- or 6-membered monocyclic aromatic heterocyclic containing one O, S or N atom; in the above substituted groups, the phenyl groups bear one or two substituents and the heterocyclic bears one substituent which may be a halogen, hydroxy, lower alkyl, lower alkoxy, lower alkylthio, cyano or nitro group;

$R^2$ represents hydrogen, lower alkyl or substituted or unsubstituted phenyl (wherein the phenyl may bear one or two of the above-mentioned substituents); and $R^3$ denotes substituted 1H-pyrazolo[3,4-b]-pyridine (Ia) or 2H-pyrazolo[3,4-b]pyridine (Ib)

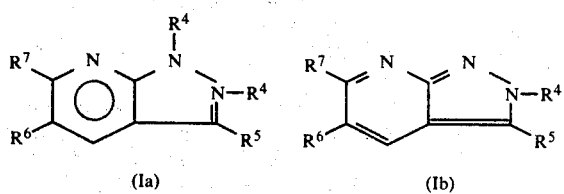

wherein $R^4$, $R^5$, $R^6$ and $R^7$ may be the same or different and each is hydrogen, lower alkyl, substituted or unsubstituted phenyl or benzyl (the phenyl or benzyl substituent where present may include any of those mentioned above with respect to $R^1$), halogen, carboxyl, or carboxylate ($COOR^8$ wherein $R^8$ is lower alkyl).

Thus, the compounds of the invention include compounds of the formulae

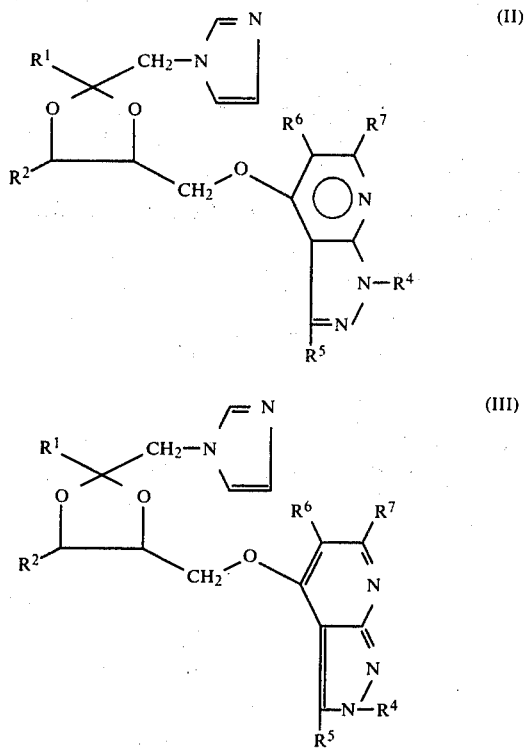

The new compounds of formula I are useful as antimicrobial agents, especially against fungi strains.

DETAILED DESCRIPTION OF THE INVENTION

The lower alkyl groups include straight or branched chain hydrocarbon groups containing 1 to 7 carbon atoms. Examples include methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio, etc. In all of these the $C_1$-$C_4$, especially $C_1$-$C_2$, lower alkyl groups are preferred.

The halogens are the four common halogens, chlorine and bromine being preferred in that order. Preferably, but not necessarily, all halogens in a single compound are the same.

The term "monocyclic aromatic heterocyclic" as used herein includes mono hetero 5- or 6-membered rings containing one hetero atom, namely, O, S or N, such as furan, pyridine and thiophene.

Preferred embodiments of this invention are compounds of formula I wherein $R^1$ is substituted phenyl, such as halophenyl or dihalophenyl, such as 2,4-dichlorophenyl, $R^2$ is hydrogen or lower alkyl, such as methyl or ethyl, $R^4$ is lower alkyl, such as methyl or ethyl, $R^5$ is hydrogen or lower alkyl, such as methyl or ethyl, $R^6$ is hydrogen or carboxyl, and $R^7$ is hydrogen, lower alkyl, such as methyl, ethyl, or phenyl, and the hydrohalide salts, such as hydrochloride salts thereof.

The compounds of formula I are prepared by etherizing the derivatives of both 1H-pyrazolo-[3,4-b]pyridines having the formula or 2H-pyrazolo[3,4-b]pyridines having the formula

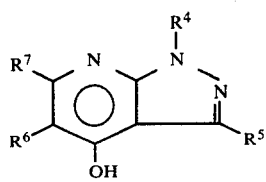

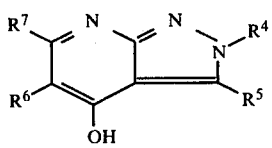

wherein $R^4$, $R^5$, $R^6$ and $R^7$ are as defined hereinbefore with an appropriate reactive ester of the formula

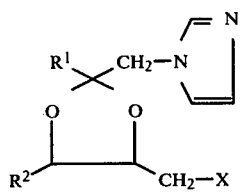

wherein X is a reactive ester function, such as mesyl, tosyl, halogen, or the like.

1,3-Dioxolanes and their reactive esters of the formula V are disclosed in the literature, for example, in J. Med. Chem. 12, 788 (1969), and 22, 1003 (1979), U.S. Pat. Nos. 4,101,664, 4,101,665 and 4,139, 540.

Pyrazolo[3,4-b]pyridines according to formula IVa and IVb, respectively, can be produced as described in J. Heterocycl. Chem. 9, 235 (1972), U.S. Pat. Nos. 4,115,394 and 4,038,283.

The compounds of formula I form salts which are also part of this invention. The salts include acid-addition salts, particularly the non-toxic, physiologically acceptable members. The bases of formula I form salts by reactions with one or more equivalents of any of a variety of the common inorganic and organic acids providing acid-addition salts including for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid-addition salts frequently provide a convenient means for isolating or purifying the product, e.g., by forming and precipitating a salt (which is not necessarily non-toxic) in an appropriate medium in which the salt is insoluble, then after separation of the salt, neutralizing with a base, such as barium hydroxide or sodium hydroxide, to obtain the free base of formula I. Other salts may then be formed from the free base by reaction with one or more equivalents of acid containing the desired acid group.

The new compounds of formula I and their salts are useful as anti-fungal and anti-bacterial agents and may be used to combat infections in various mammalian species, such as mice, rats, dogs, guinea pigs and the like, particularly those due to organisms, such as *Candida albicans*, as well as organisms, such as *Trichomonas vaginalis* or *Trichophyton mentagrophytes*. For example, a compound or mixture of compounds of formula I or physiologically acceptable acid-addition salt thereof can be administered orally to an infected animal, e.g., to a mouse, in an amount of about 5 to 25 mg per kg per day in 2 to 4 divided doses. These may be conventionally formulated in a tablet, capsule or elixir containing about 10 to 250 mg per dosage unit, by compounding the active substance or substances with the conventional excipient, vehicle, binder, preservative, flavor, etc., as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following Examples represent preferred embodiments of the present invention. Temperatures are in degrees Celsius.

EXAMPLE 1

4-[[2-(2,4-Dichlorophenyl)-2-(1H-imidazol-1-yl-methyl)-1,3-dioxolan-4-yl]methoxy]-2-methyl-6-phenyl-2H-pyrazolo[3,4-b]pyridine A mixture consisting of 1.24 g of 2-methyl-6-phenyl-2H-pyrazolo[3,4-b]pyridine-4-ol (5.5 mmoles), 40 ml of dry dimethylsulfoxide, 12 ml of dry benzene and 0.28 g of sodium hydride dispersion 55% (in mineral oil) (6.5 mmoles) is stirred at 40° C. for one hour. After addition of 2.04 g of cis-2-(2,4-dichlorophenyl)-2-(1H-imidazol-1-ylmethyl)-1,3-dioxolan-4-ylmethyl methanesulfonate (5 mmoles) the mixture is stirred at 105° C. for 18 hours. Then the reaction mixture is evaporated in vacuo and the residue is treated with water and chloroform. The chloroform layer is dried, charcoaled and subsequently evaporated. The foam-like solidified product (2.6 g) is triturated with ether to become crystalline. Recrystallization of the filtered off product from methylisobutyl ketone yields the pure title compound (0.9 g), m.p. 227°–229°.

Evaporation of the mother liquor, trituration of the residue with ether and recrystallization of the obtained product gives an additional crop of 0.2 g. Total yield 1.1 g (40%).

EXAMPLE 2

4-[[2-(2,4-Dichlorophenyl)-2-(1H-imidazol-1-ylmethyl)-1,3-dioxolan-4-yl]methoxy]-1-ethyl-3,6-dimethyl-1H-pyrazolo3,4-b]pyridine, hydrochloride, hydrate (1:2:1)

To a stirred solution of 48 ml of dry dimethylsulfoxide and 15 ml of dry benzene are added 0.34 g of sodium hydride dispersion 55% (in mineral oil) (7.8 mmoles) and 1.26 g of 1-ethyl-3,6-dimethyl-1Hpyrazolo[3,4-b]pyridin-4-ol (6.6 mmoles) and the whole is kept at 40° C. for one hour. After addition of 2.44 g of cis-2-(2,4-dichlorophenyl)-2-(1H-imidazol-1-ylmethyl)-1,3-dioxolan-4-ylmethylmethanesulfonate (6 mmoles), the reaction mixture is stirred for additional 18 hours at 105° and then evaporated in vacuo. The residue is triturated with water and chloroform. The separated chloroform layer is evaporated and the oily residue again taken up in ether. The ethereal extract is dried, charcoaled, filtered and then ethereal hydrochloric acid is added to give an oily hydrochloride. To get it crystalline the ether is decanted and the hydrochloride treated twice with fresh ether and finally with a few milliliters of acetonitrile. 1.89 g of the resulting crystalline product melt at 205°–206°. Recrystallization from acetonitrile yields 1.11 g (31%) of the pure title compound, m.p. 215°–216°.

EXAMPLE 3

4-[[2-(2,4-Dichlorophenyl)-2-(1H-imidazol-1-ylmethyl)-1,3-dioxolan-4-yl]methoxy]-2-methyl-2H-pyrazolo[3,4-b]pyridine-5-carboxylic acid, hydrochloride, hydrate (2:2:1)

By repeating the procedure of Example 1 but substituting for 2-methyl-6-phenyl-2H-pyrazolo[3,4-b]pyridin-4-ol used therein an equivalent amount of 4-hydroxy-2-methyl-2H-pyrazolo-[3,4-b]pyridine-5-carboxylic acid ethyl ester, the title compound is accessible.

For preparing the hydrochloride salt, the oily base in chloroform is evaporated in vacuo and again taken up in a small amount of acetonitrile. Addition of ethereal hydrochloric acid separates an oily hydrochloride, which, after decanting of the solvent, is recrystallized from water; m.p. 268°–269°, yield 43%.

EXAMPLES 4 TO 29

The following additional products of formula III are obtained by the procedure of Example 1 by employing as starting materials the 1H-pyrazolo-[3,4-b]pyridine of formula IVb and the reactive ester of formula V set out below.

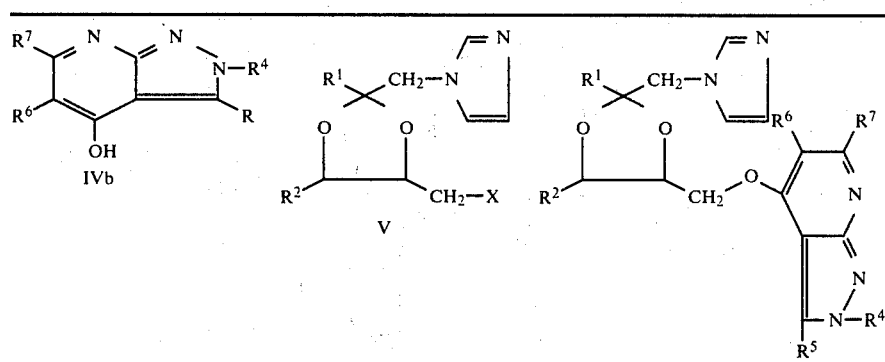

| Ex. No. | $R^1$ | $R^2$ | $R^4$ | $R^5$ | $R^6$ | $R^7$ |
|---|---|---|---|---|---|---|
| 4. | $C_6H_5$ | H | H | H | H | H |
| 5. | H | $CH_3$ | $CH_3$ | H | $C_6H_5$ | Cl |
| 6. | $CH_3$ | $CH_3$ | $C_6H_5$ | Cl | H | Cl |
| 7. | $C_2H_5$ | $C_6H_5$ | p-$BrC_6H_4CH_2$ | $C_2H_5$ | Br | $C_6H_5$ |
| 8. | $C_6H_5CH_2$ | H | H | $C_6H_5$ | COOH | Cl |
| 9. | p-$CH_3OC_6H_4CH_2$ | $C_2H_5$ | $CH_3$ | Br | $COOCH_3$ | H |
| 10. | o-$ClC_6H_4CH_2$ | $C_6H_5$ | $C_6H_5$ | $C_2H_5$ | H | COOH |
| 11. | m-$OHC_6H_4CH_2$ | H | H | H | o-$ClC_6H_4$ | $COOC_2H_5$ |
| 12. | o-$CH_3SC_6H_4CH_2$ | H | p-$OHC_6H_4$ | $CH_3$ | H | H |
| 13. | p-$CNC_6H_4CH_2$ | $C_3H_7$ | COOH | H | $CH_3$ | H |
| 14. | p-$NO_2C_6H_4CH_2$ | $C_6H_5$ | $CH_3$ | COOH | H | $C_2H_5$ |
| 15. | p-$CH_3C_6H_4$ | H | $COOCH_3$ | H | Cl | $CH_3$ |
| 16. | o-$ClC_6H_4$ | $CH_3$ | $C_6H_5CH_2$ | $COOC_2H_5$ | H | $C_2H_5$ |
| 17. | m-$OHC_6H_4$ | H | H | m-$CH_3C_6H_4$ | H | Br |
| 18. | o-$CH_3SC_6H_4$ | $C_6H_5$ | H | H | Cl | H |
| 19. | p-$CNC_6H_4$ | o-$ClC_6H_4$ | $CH_3$ | H | H | H |
| 20. | p-$NO_2C_6H_4$ | m-$CH_3OC_6H_4$ | H | $C_2H_5$ | Br | H |
| 21. | 2,4-di-$ClC_6H_3$ | p-$OHC_6H_4$ | $C_6H_5$ | $C_2H_5$ | H | Cl |
| 22. | 2,4-di-$CH_3C_6H_3$ | o-$NO_2C_6H_4$ | $CH_3$ | $C_6H_5$ | $CH_3$ | H |
| 23. | ![furyl] | H | H | $CH_3$ | H | $CH_3$ |
| 24. | ![thienyl] | $CH_3$ | $C_6H_5$ | H | Br | H |
| 25. | ![pyrrolyl] | $C_6H_5$ | $CH_3$ | $C_6H_5$ | Cl | H |
| 26. | H | H | H | H | H | H |
| 27. | $CH_3$-furyl | H | m-$ClC_6H_4CH_2$ | Cl | H | H |
| 28. | Cl-thienyl | $CH_3$ | $C_6H_5$ | H | H | $C_6H_5$ |
| 29. | HO-pyridyl | $CH_3$ | $CH_3$ | $CH_3$ | $CH_3$ | $CH_3$ |

The following additional products of formula II are obtained by the procedure of Example 2 by employing as starting materials the 2H-pyrazolo[3,4-b]pyridine of formula IVa and the reactive ester of formula V set out below.

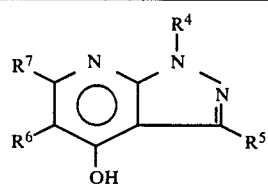

IVa

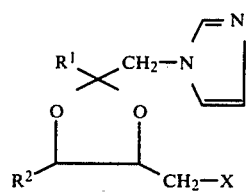

V

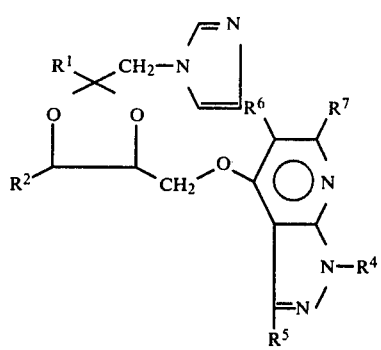

II

| Ex. No. | $R^1$ | $R^2$ | $R^4$ | $R^5$ | $R^6$ | $R^7$ |
|---|---|---|---|---|---|---|
| 30. | $C_6H_5$ | H | H | H | H | H |
| 31. | H | $CH_3$ | $CH_3$ | H | $C_6H_5$ | Cl |
| 32. | $CH_3$ | $CH_3$ | $C_6H_5$ | Cl | H | Cl |
| 33. | $C_2H_5$ | $C_6H_5$ | o-$BrC_6H_4CH_2$ | $C_2H_5$ | Br | $C_6H_5$ |
| 34. | $C_6H_5CH_2$ | H | H | $C_6H_5$ | COOH | Cl |
| 35. | p-$CH_3OC_6H_4CH_2$ | $C_2H_5$ | $CH_3$ | Br | $COOCH_3$ | H |
| 36. | o-$ClC_6H_4CH_2$ | $C_6H_5$ | $C_6H_5$ | $C_2H_5$ | H | COOH |
| 37. | m-$OHC_6H_4CH_2$ | H | H | H | o-$ClC_6H_4$ | $COOC_2H_5$ |
| 38. | o-$CH_3SC_6H_4CH_2$ | H | p-$OHC_6H_4$ | $CH_3$ | H | H |
| 39. | p-$CNC_6H_4CH_2$ | $C_3H_7$ | COOH | H | $CH_3$ | H |
| 40. | p-$NO_2C_6H_4CH_2$ | $C_6H_5$ | $CH_3$ | COOH | H | $C_2H_5$ |
| 41. | p-$CH_3C_6H_4$ | H | $COOCH_3$ | H | Cl | $CH_3$ |
| 42. | o-$ClC_6H_4$ | $CH_3$ | $C_6H_5CH_2$ | $COOC_2H_5$ | H | $C_2H_5$ |
| 43. | m-$OHC_6H_4$ | H | H | m-$CH_3OC_6H_4$ | H | Br |
| 44. | o-$CH_3SC_6H_4$ | $C_6H_5$ | H | H | Cl | H |
| 45. | p-$CNC_6H_4$ | o-$ClC_6H_4$ | $CH_3$ | H | H | H |
| 46. | p-$NO_2C_6H_4$ | m-$CH_3OC_6H_4$ | H | $C_2H_5$ | Br | H |
| 47. | 2,4-di-$ClC_6H_3$ | p-$OHC_6H_4$ | $C_6H_5$ | $C_2H_5$ | H | Cl |
| 48. | 2,4-di-$CH_3C_6H_3$ | o-$NO_2C_6H_4$ | $CH_3$ | $C_6H_5$ | $CH_3$ | H |
| 49. | furyl | H | H | $CH_3$ | H | $CH_3$ |
| 50. | thienyl | $CH_3$ | $C_6H_5$ | H | Br | H |
| 51. | pyridyl | $C_6H_5$ | $CH_3$ | $C_6H_5$ | Cl | H |
| 52. | H | H | H | H | H | H |
| 53. | $CH_3$-furyl | H | p-$BrC_6H_4CH_2$ | Cl | H | H |
| 54. | Cl-thienyl | $CH_3$ | $C_6H_5$ | H | H | $C_6H_5$ |
| 55. | HO-pyridyl | $CH_3$ | $CH_3$ | $CH_3$ | $CH_3$ | $CH_3$ |

What is claimed is:

1. A compound of the formula

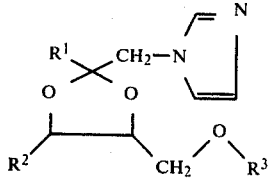

wherein R¹ is hydrogen; lower alkyl containing 1 to 7 carbon atoms; substituted or unsubstituted phenyl-lower alkyl containing 1 to 7 carbon atoms in the lower alkyl group, and wherein the phenyl group in the above may bear zero, one or two halogen, hydroxy, lower alkyl containing 1 to 7 carbon atoms, lower alkylthio containing 1 to 7 carbon atoms, lower alkoxy containing 1 to 7 carbon atoms, cyano and/or nitro groups; substituted or unsubstituted phenyl, wherein the phenyl group in the above may bear zero, one or two halogen, hydroxy, lower alkyl containing 1 to 7 carbon atoms, lower alkylthio containing 1 to 7 carbon atoms, lower alkoxy containing 1 to 7 carbon atoms, cyano and/or nitro groups; substituted or unsubstituted 5- or 6-membered monocyclic aromatic heterocyclic containing one O, S or N atom selected from the group consisting of furan, pyridine and thiophene, wherein the heterocyclic may bear zero or one halogen, hydroxy, lower alkyl containing 1 to 7 carbon atoms, lower alkylthio containing 1 to 7 carbon atoms, lower alkoxy containing 1 to 7 carbon atoms, cyano or nitro group;

R² is hydrogen, lower alkyl containing 1 to 7 carbon atoms, or phenyl;

R³ is

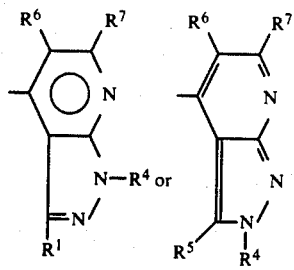

wherein R⁴, R⁵, R⁶ and R⁷ may be the same or different and each is hydrogen, lower alkyl containing 1 to 7 carbon atoms, halogen, carboxyl, COO-lower alkyl containing 1 to 7 carbon atoms, phenyl, benzyl, or phenyl or benzyl substituted with one or two halogen, hydroxy, lower alkyl containing 1 to 7 carbon atoms, lower alkylthio containing 1 to 7 carbon atoms, lower alkoxy containing 1 to 7 carbon atoms, cyano and/or nitro groups; and physiologically acceptable acid-addition salts thereof.

2. The compound of claim 1 wherein R³ is

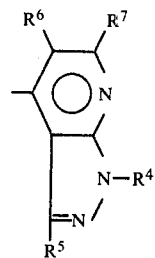

3. The compound of claim 1 wherein R³ is

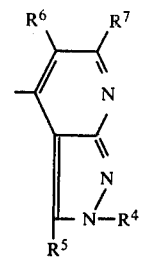

4. The compound of claim 1 wherein R¹ is phenyl, halophenyl or dihalophenyl.

5. The compound of claim 1 wherein R² is hydrogen.

6. The compound of claim 2 wherein R⁷ is hydrogen, phenyl or lower alkyl, R⁶ is hydrogen or carboxyl, R⁴ is lower alkyl and R⁵ is hydrogen or lower alkyl.

7. The compound of claim 3 wherein R⁷ is hydrogen, phenyl or lower alkyl, R⁶ is hydrogen or carboxyl, R⁴ is lower alkyl and R⁵ is hydrogen or lower alkyl.

8. The compound of claim 1 in the form of its hydrochloride salt.

9. The compound of claim 1 having the name 4-[[2-(2,4-dichlorophenyl)-2-(1H-imidazol-1-ylmethyl)-1,3-dioxolan-4-yl]methoxy]-2-methyl-6-phenyl-2H-pyrazolo[3,4-b]pyridine, or its hydrochloride salt.

10. The compound of claim 1 having the name 4-[[2-(2,4-dichlorophenyl)-2-(1H-imidazol-1-ylmethyl)-1,3-dioxolan-4-yl]methoxy]-1-ethyl-3,6-dimethyl-1H-pyrazolo[3,4-b]pyridine, or its hydrochloride salt.

11. The compound of claim 1 having the name 4-[[2-(2,4-dichlorophenyl)-2-(1H-imidazol-1-ylmethyl)-1,3-dioxolan-4-yl]methoxy]-2-methyl-2H-pyrazolo-[3,4-b]pyridine-5-carboxylic acid, or its hydrochloride salt.

12. An antimicrobial composition comprising an antimicrobial amount of a compound as defined in claim 1 and a pharmaceutically acceptable carrier therefor.

13. A method for treating bacterial or fungal infections in mammals which comprises administering to a mammalian host an antibacterial or antifungal effective amount of a compound as defined in claim 1.

* * * * *

UNITED STATES PATENT AND TRADEMARK OFFICE
CERTIFICATE OF CORRECTION

PATENT NO. : 4,260,614
DATED : April 7, 1981
INVENTOR(S) : Hans Hoehn

It is certified that error appears in the above-identified patent and that said Letters Patent are hereby corrected as shown below:

On the title page, the title should read --4-[2-(1H-IMIDAZOL-1-YLMETHYL)-1,3-DIOXOLAN-4-YL]METHOXYPYRAZOLO[3,4-b]PYRIDINES--.
Column 1, the title should read --4-[2-(1H-IMIDAZOL-1-YLMETHYL)-1,3-DIOXOLAN-4-YL]METHOXYPYRAZOLO[3,4-b]PYRIDINES--.
Column 1, formula (Ia) should read

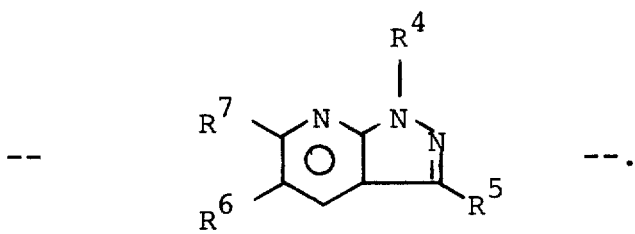

Column 4, line 47, "3,4-b" should read --[3,4-b--.
Column 4, line 51, "1Hpyrazolo" should read --1H-pyrazolo--.

Signed and Sealed this

Fourth Day of August 1981

[SEAL]

Attest:

GERALD J. MOSSINGHOFF

Attesting Officer        Commissioner of Patents and Trademarks